United States Patent [19]

Ries et al.

[11] Patent Number: 5,782,928
[45] Date of Patent: Jul. 21, 1998

[54] ACETABULAR CUP BODY PROSTHESIS

[75] Inventors: Michael D. Ries, Cooperstown, N.Y.; Brian Austin, Germantown, Tenn.; David L. Evans, Bartlett, Tenn.; Steve Miller; Jeff Shea, both of Memphis, Tenn.

[73] Assignee: Smith & Nephew, Inc., Memphis, Tenn.

[21] Appl. No.: 735,516

[22] Filed: Oct. 23, 1996

Related U.S. Application Data

[63] Continuation-in-part of Ser. No. 563,219, Nov. 27, 1995, Pat. No. 5,676,704.

[51] Int. Cl.⁶ .................................................. A61F 2/34
[52] U.S. Cl. ............................................................ 623/22
[58] Field of Search .......................... 606/80; 623/16, 623/18, 22, 23

[56] References Cited

U.S. PATENT DOCUMENTS

| | | | |
|---|---|---|---|
| 3,939,497 | 2/1976 | Heimke et al. | 3/1.912 |
| 4,241,463 | 12/1980 | Khovaylo | 3/1.913 |
| 4,666,448 | 5/1987 | Ganz | 623/22 |
| 4,685,923 | 8/1987 | Mathys | 623/22 |
| 4,695,282 | 9/1987 | Forte et al. | 623/22 |
| 4,704,127 | 11/1987 | Averill et al. | 623/22 |
| 4,792,337 | 12/1988 | Müller | 623/22 |
| 4,795,470 | 1/1989 | Goyman et al. | 623/22 |
| 4,798,610 | 1/1989 | Averill et al. | 623/22 |
| 4,813,959 | 3/1989 | Cremascoli | 623/22 |
| 4,828,565 | 5/1989 | Duthoit et al. | 623/22 |
| 4,892,549 | 1/1990 | Figgie, III et al. | 623/22 |
| 5,211,665 | 5/1993 | Ku | 623/22 |
| 5,358,532 | 10/1994 | Evans et al. | 623/22 |
| 5,443,519 | 8/1995 | Averill et al. | 623/22 |
| 5,514,141 | 5/1996 | Prizzi, Jr. | 606/80 |

FOREIGN PATENT DOCUMENTS

| | | |
|---|---|---|
| 0 013 863 | 8/1980 | European Pat. Off. . |
| 0 169 978 | 2/1986 | European Pat. Off. . |
| 0 091 315 | 7/1986 | European Pat. Off. . |
| 0 211 169 | 2/1987 | European Pat. Off. . |
| 0 212 087 | 3/1987 | European Pat. Off. . |
| 0 285 756 | 10/1988 | European Pat. Off. . |
| 0 327 509 | 5/1991 | European Pat. Off. . |
| 3341723 C1 | 3/1985 | Germany . |
| WO95/16413 | 6/1995 | WIPO . |

OTHER PUBLICATIONS

Osteonics The Science of Better Fit Brochure, Secur-Fit HA PSL Acetabular Shells, Hydroxylapatite Coated Shells, 2 pages.

*Primary Examiner*—David Isabella
*Attorney, Agent, or Firm*—Pravel, Hewitt, Kimball & Krieger

[57] ABSTRACT

An improved acetabular cup prosthesis has a cup body with inner convex and outer concave surfaces. The cup body has an apex and a base that defines a plane. The cup body outer convex surface has a toroidally shaped portion between the base and the transition. In one embodiment, the outer convex surface is toroidally shaped between the rim and a distance about one third of the distance of the rim to the apex. In another embodiment, a plurality of cup bodies are provided in a range of sizes between about 40 mm and 80 mm. Each cup body has a companion rotary reamer that is correspondingly shaped. The companion cup body is oversized between about 1 mm and 3 mm so that a generally constant change in volume is provided for all cup sizes between 40 mm and 80 mm.

22 Claims, 5 Drawing Sheets

ACETABULAR CUP BODY PROSTHESIS

CROSS REFERENCE TO RELATED APPLICATIONS

This is a continuation-in-part of U.S. patent application Ser. No. 08/563,219, filed Nov. 27, 1995, now U.S. Pat. No. 5,676,704 which is incorporated herein by reference.

BACKGROUND OF THE INVENTION

1. Field of the Invention

The present invention relates to orthopedic prosthetic devices and more particularly to an improved orthopedic prosthesis (and a method of surgically implanting the prosthesis), wherein the prosthesis is in the form of a cup shaped body having in inner concave surface, an outer convex surface, and an annular rim that defines a plane, and wherein all or majority of the outer convex surface define a toroidal shape that can form an interference fit with a purely hemispherical socket that is surgically prepared, and wherein the amount of interference fit is proportional with cup diameter.

2. General Background

There are a number of commercially available acetabular prosthetic devices that include a cup shaped body. Some of these acetabular cups have correspondingly shaped inner and outer concave and convex surfaces. Some acetabular cup devices have outer surfaces with two differently shaped regions thereon including an annular rim or skirt that is thickened for forming an interference fit with the pelvis. Another acetabular cup (Patent DE 3341723C1) is in the form of a hemispherical socket body that is flattered at the crown region, to ensure lateral wedging of the socket in the pelvic bone.

Another patented cup design is seen in the Averill U.S. Pat. No. 4,704,127 entitled "Dual-Geometry Acetabular Cup Component and Method of Implant". The '127 patent provides a cup with a shell component having an outer surface that includes a frustro-conical surface portion and a spherical surface portion. As part of the method, the patient's acetabulum is prepared with an inner surface that includes a frustro-conical surface portion and a spherical surface portion, the spherical surface portions having essentially the same radius and the frustro-conical surface portions having relative dimensions such that upon nesting of the spherical surface portions in contiguous relationship, the frustro-conical portions engage one another in an interference fit to secure the shell component within the prepared acetabulum.

The Figgie U.S. Pat. No. 4,892,549 discloses an acetabular cup that has a shell component with an outer surface including a first spherical surface portion and a second spherical surface portion, and an acetabulum is prepared with an inner surface having a spherical configuration complimentary to the second spherical surface portion of the shell component. The radius of the first spherical surface portion is slightly greater than the radius of the second spherical surface portion such that upon nesting of the second spherical surface portion of the shell component in contiguous relationship with the inner surface of the acetabulum, the first spherical surface portion engages the inner surface of the acetabulum in an interference fit to secure the shell component within the prepared acetabulum.

Some acetabular cup devices have projections extending from the outer surface of the cup-shaped body for engaging the surrounding pelvic bone tissue. For example, U.S. Pat. No. 3,939,497 describes a socket for a hip joint prosthesis which is secured to a cavity in the bone tissue by a series of radially arranged pegs which can be projected outwardly from the wall of the socket into the surrounding tissue by a central screw which also has a self-tapping thread that enters the tissue.

U.S. Pat. No. 4,685,923 discloses a hip joint socket made from a plastic material that can be installed without the use of bone cement or adhesive. The socket comprises a hemisphere of polyethylene.

The Forte et al. U.S. Pat. No. 4,695,282 discloses an acetabular cup assembly that includes a metal shell component and a plastic bearing insert capable of assembly intraoperatively, the metal shell component being secured in position within the acetabulum and then the plastic bearing insert being receivable within the shell component. The shell component has an outer surface that includes a generally spherically shaped portion and a generally frustro-conically shaped second surface portion. An annular shoulder forms a connection between the two different outer surfaces of the shell.

The Cremascoli U.S. Pat. No. 4,813,959 discloses a total hip prosthesis structure that includes an acetabular or socket component and a femoral or pin component, the two components being made of a metal or a metal alloy and being intimately connected to parts of ceramic material at least part of the surface of which is granular or porus so as to encourage osteogenesis after implantation. The metal part of the acetabular component is shaped in such a way as to simplify and facilitate its anchorage in a corresponding cavity of the ilium by having a sharp screw thread thereon.

In U.S. Pat. No. 4,792,337 an acetabular cup is provided which has a metallic shell. The cup is for cement-less fixation in the acetabulum.

In U.S. Pat. No. 4,828,565 there is provided a component for a non-cemented hip prosthesis. The component has two parts, a titanium hemispherical shell and a cup of polymer which is engaged into it.

Another acetabular cup for cement-less fixation in the acetabulum is described in European Patent Application No. 13,863, published Jun. 8, 1980.

European Patent Application No. 169,978 published May 2, 1986, describes an acetabular cup which has an outer shell embedded into the patient's pelvis. The outer shell has a frustro-conical skirt and a spherical central cap.

In European Patent Application No. 211,169 published Feb. 25, 1987, an acetabular cup is described in which an external boss protrudes from the outer surface of the acetabulum body to fit into a pre-drilled hole in the acetabulum.

Other foreign patents and patent applications which describe acetabular cups include European Patent Application No. 212,087 published Apr. 3, 1987, wherein metallic pins project from the surface of the cup and contain holes in which tissue may grow. In European Patent No. 341,198 published Nov. 8, 1989, an acetabular cup has a metal outer shell and a plastic body for retaining the hip joint head.

A PCT publication WO 95/16413 discloses a hip cup for use as an acetabular component in a hip prosthesis. The prosthesis comprises a shell part having an at least partially convex outer surface. The shell part is insertable into a cavity having an inner surface that is substantially defined by the outer surface of a segment of this sphere. The outer surface of the shell part substantially corresponds to the outer surface of a part of an ellipsoid, the arrangement being such that during positioning the shell part contacts the longitudinal edge of the cavity at least by a circumferential edge, while a space is formed between the inner surface of the cavity and the apex of the shell part.

Two recent U.S. Patents have issued for acetabular cup components. The Averill U.S. Pat. No. 5,443,519 discloses an acetabular cup prosthetic device comprised of an outer shell component and an inner bearing insert and a method of implanting the acetabular cup prosthetic within a patient. The outer surface of the shell has a plurality of region in which conform to the curvature of at least one ellipsoid.

The Evans U.S. Pat. No. 5,358,532 entitled "CEMENTLESS ACETABULAR CUP" provides a component that is press fit into a patient's acetabulum to create an interference fit and to eliminate the need for cement. A body portion of the cup provides an outer convex surface. The inside of the cup provides an inner concave surface. An apex portion of the cup or shell is spaced from the lower rim portion, the rim defining a plane. A plurality of annular rings are spaced along the body outer surface beginning at the lower rim and extending at least a partial distance toward the apex. Each of the annular rings is preferably generally parallel to the plane of the lower rim. Three recently issued European patents disclose other examples of acetabular prosthetic components. These include European patents specifications 0091315, 0285756, and 0327509.

SUMMARY OF THE PRESENT INVENTION

The present invention provides an acetabular cup prosthesis that includes a surgically implantable acetabular cup body having an inner concave surface and an outer convex surface adapted to interface with a reamed, hemispherical socket of a patient's pelvic bone tissue.

In the preferred embodiment, the pelvic bone tissue is prepared by providing a shaped, reamed socket using a single step reaming process into which the acetabular cup body is fitted during the surgical procedure.

The cup body provides an apex and a base in the form of an annular rim that has a radius and a center as origin for the radius. The origin is positioned on a plane that is defined by the annular rim.

In another embodiment, the cup body has an outer convex surface that is toroidally shaped between the apex and the rim.

In one embodiment, the toroidally shaped portion extends between the base and a position near but shaped from the apex.

In one embodiment, the toroidally shaped portion extends from the base to a position about two thirds of the distance of the base to the apex.

The toroidal shape is defined by curve line that extends from the apex to the rim and having a radius of curvature of preferably smaller than the apical radius with an origin for the radius that is spaced about 2 millimeters from the cup rim center, such that the outer diameter of the torus is greater than the apical diameter.

The curve line is then generated 360° to generate the toroidal surface in one embodiment.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 4 is a side sectional view of a fourth preferred embodiment of the apparatus of the present invention; and FIG. 5 is a top view of the embodiment of FIG. 4;

DETAILED DESCRIPTION OF THE PREFERRED EMBODIMENT

Figure 1:
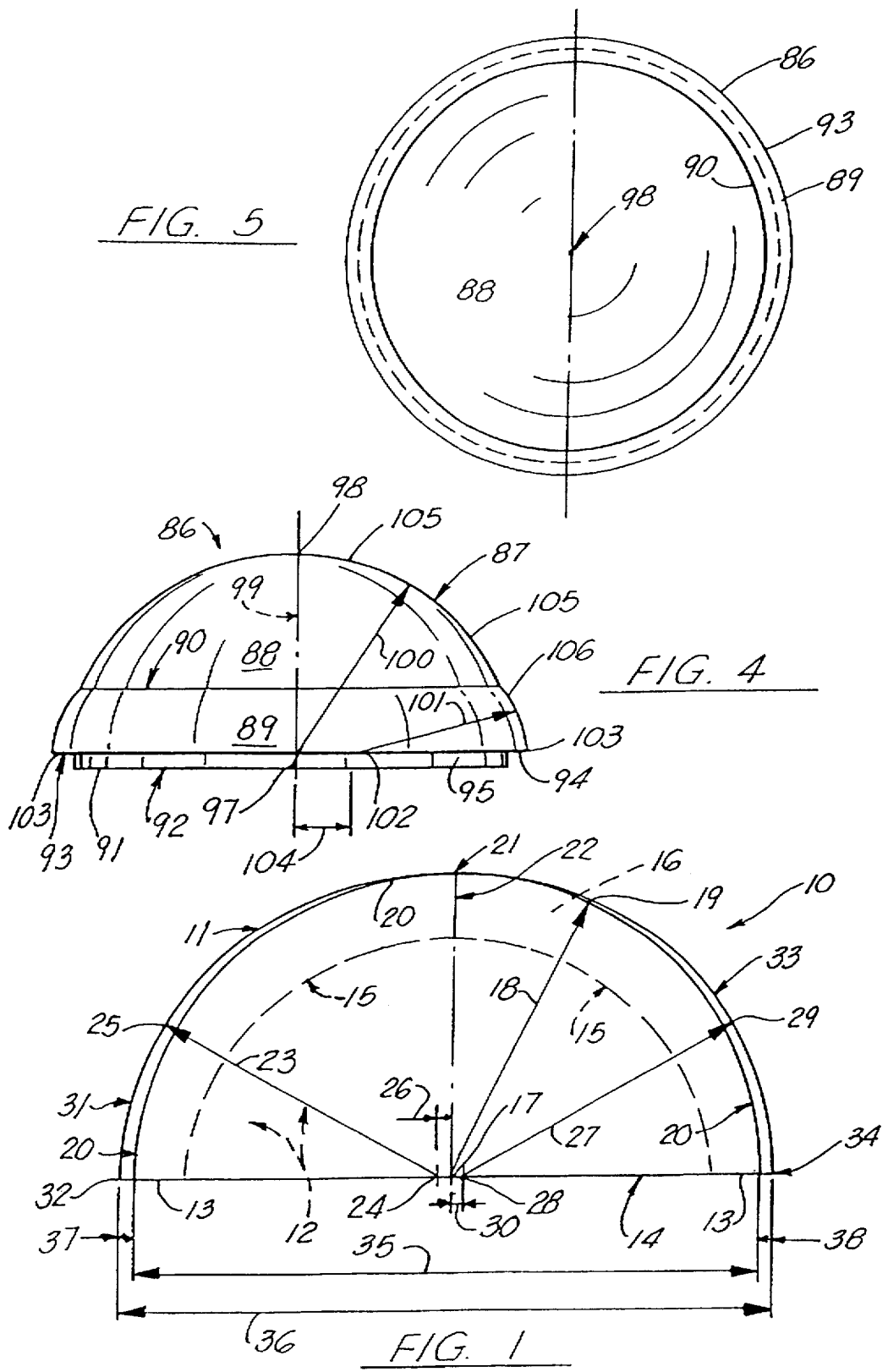
FIG. 1 is a perspective view of a first embodiment of the apparatus of the present invention.

FIG. 1 shows the preferred embodiment of the apparatus of the present invention designated generally by the numeral 10. Acetabular cup prosthesis 10 is in the form of a cup body having an outer convex surface 11, a concavity 12 for receiving a polyethylene liner and the ball of a femoral implant, and annular rim 13 that is generally flat to define base plane 14.

The cup prosthesis 10 includes a concave surface 15 that surrounds the concavity 12. The cup 10 is in the form of a body defined by cup wall 16. The interior concavity 12 can be generally hemispherically shaped, as defined by inner surface 15. The outer convex surface 11 is not completely hemispherically shaped, but rather has a toroidal shape.

Annular rim 13 is a flat rim that is circular in shape, having an origin 17 that falls in base plane 14. A purely hemispherical shape is illustrated by radial line 18 having one end portion at origin 17 and its opposite end portion at terminal 19. If the radial line 18 is rotated and about origin 17, a purely hemispherical shape is generated, designated by the curve line 20 in FIG. 1. Line 22 is also a radial line that extends from origin 17 to cup apex 21. The line 22 is perpendicular to plane 14.

Outer surface 11 is a toroidally shaped surface. When compared to hemispherical curved line 20, the toroidal outer surface 11 of the cup 10 gradually thickens continuously from apex 21 toward points 32 and 34. If the surgeon prepares a pure hemispherically shaped socket at the patient's acetabulum using a reamer, the prosthesis 10 will form an interference fit with such a hemispherical socket due to this ever thickening geometry and toroidal shape of outer surface 11 as shown in FIG. 1. A purely hemispherically shaped cup 10 is tracked by the curved line 20 and has diameter defined by the arrow 35 in FIG. 1. The toroidally shaped cup outer surface 11 of the present invention has a diameter defined by the arrow 36, thus showing a thickened region when compared to hemispherical diameter 35 the thickened region is designated by the arrows 37 and 38 in FIG. 1.

The toroid shaped cup 10 will form an interference fit with a hemispherically shaped, surgically prepared socket having a size and shape as tracked by curved line 20 in FIG. 1 and having diameter 35.

To define the toroidal shape of outer surface 11, a pair of reference lines 23, 27 are shown in FIG. 1. The reference line 23 is a radial line having a beginning point 24 that lies in base plane 14 and which is spaced from origin 17 by a measure designated as arrow 26. Line 23 terminates at terminal 25. In FIG. 1, a second reference line 27 is a radial line beginning at 28 and ending at terminal 29. The line 27 is spaced from origin 17 by a measure designated as 30 in FIG. 1.

When rotated between the point 32 and apex 21, the radial reference line 23 generates a curved line 31 extending between the point 32 at rim 13 and the cup apex 21. Similarly, the reference radial line 27 generates a curved line 33 beginning at point 34 on rim 13 and ending at apex 21. The lines 31, 33 generate a toroidal outer surface 11 when rotated 360° about central axial line 22.

Figure 2:
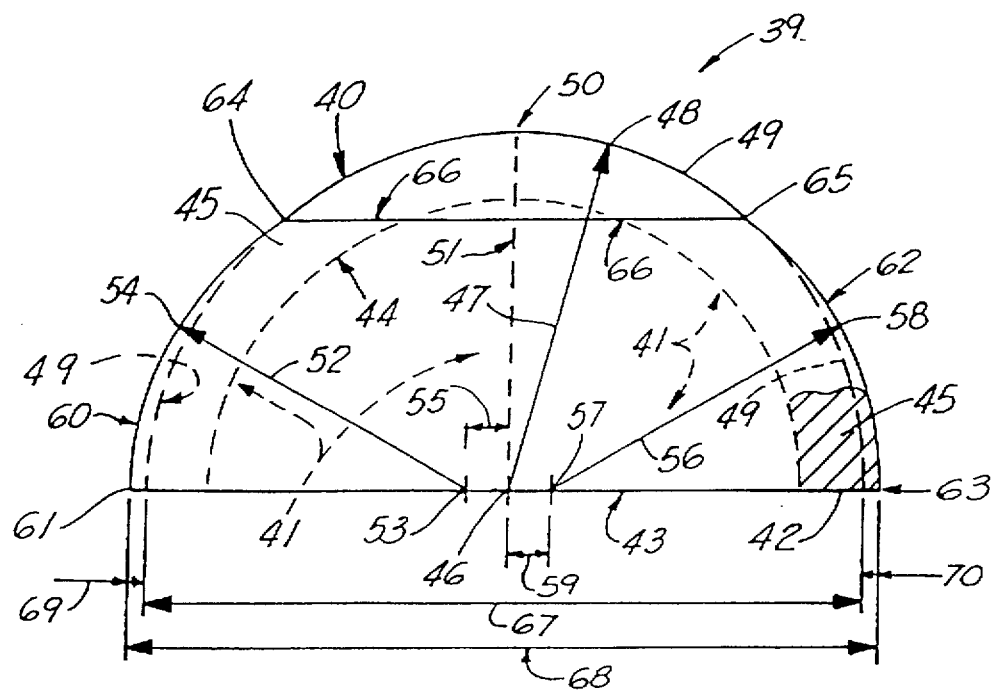
FIG. 2 is a side sectional view of a second embodiment of the apparatus of the present invention.

FIG. 2 designates a second embodiment of acetabular cup prosthesis of the present invention designated generally by the numeral 39. Cup prosthesis 39 has a convex surface 40, a concavity 41 for receiving a polyethylene liner and then a hip prosthesis ball for example, and an annular rim 42 that defines a base plane 43. The cup prosthesis 39 has a concave surface 44 and a cup wall 45. The annular rim 42 is circular, having an origin 46 that falls in base plane 43. Prosthesis 39 includes a concave surface 44 that communicates with annular rim 42. The cup wall 45 extends around the concavity 41. Annular rim 42 is generally circular, having an origin 46. A radial line 47 extends from origin 46 to a terminal point 48 as shown. The radial 47, when rotated about origin 46 produces a hemispherical curved portion between points 64 and 65. This curved portion is designated as 49 in FIG. 2. A reference line 51 extending between origin 46 and along a line perpendicular to plane 43 defines a radial line that communicates with apex 50 of cup 39.

A pair of radial lines 52, 56 are also seen in FIG. 2. Each of these radial lines 52, 56 has a beginning point 53, 57 respectively that is spaced from origin 56. The distance of spacing is designated respectively by the arrows 55, 59 in FIG. 2.

If reference lines 52 and 56 are rotated respectively about their beginning points 53, 57, the terminal end point 54, 58 respectively of each radial line 52, 56 tracks a curved line that tracks between points 64 and 65 to point 61 and 63. The curved line generated by radial line 52 is designated as 60 in FIG. 2. The curved line that is generated by radial line 56 is designated as 62 in FIG. 2. These curved lines 60, 62 extend between the beginning points 61, 63 and end at annular reference line 66. In the elevational view of FIG. 2, points 64 and 65 fall on annular reference line 66. Curved lines 60, 62 define a toroidal portion of cup prosthesis 39 when rotated 360° about hemispherical line 51. Curved line 49 is a portion of cup prosthesis 39. When radius 47 is rotated beyond the reference line 66 toward points of beginning 61, 63, a purely hemispherically shaped curved line would be produced that is designated by the numeral 49 which is a phantom line below annular reference line 66 as shown in FIG. 2. Thus, the portion of cup 39 that extends beyond the phantom lines 49 and which is tracked by the curved line 60, 62 represents a thickened area of the cup wall 45 that can be used to form an interference fit with a hemispherically shaped socket formed in the patient's acetabulum. The line 49 in FIG. 2 represents the shape of the opening that would be formed in the patient's acetabulum prior to the placement of cup prosthesis 39.

In FIG. 2, the diameter of the surgically formed opening is designated by the arrow 67. The arrow 68 defines the thickness or diameter of cup prosthesis 39. The arrows 69 and 70 thus designated the thickened portion of the cup wall 45 that is wedged into the surgically formed opening for creating an interference fit upon placement of the cup prothesis 39 into the surgically formed, hemispherically shaped cavity.

Figure 3:
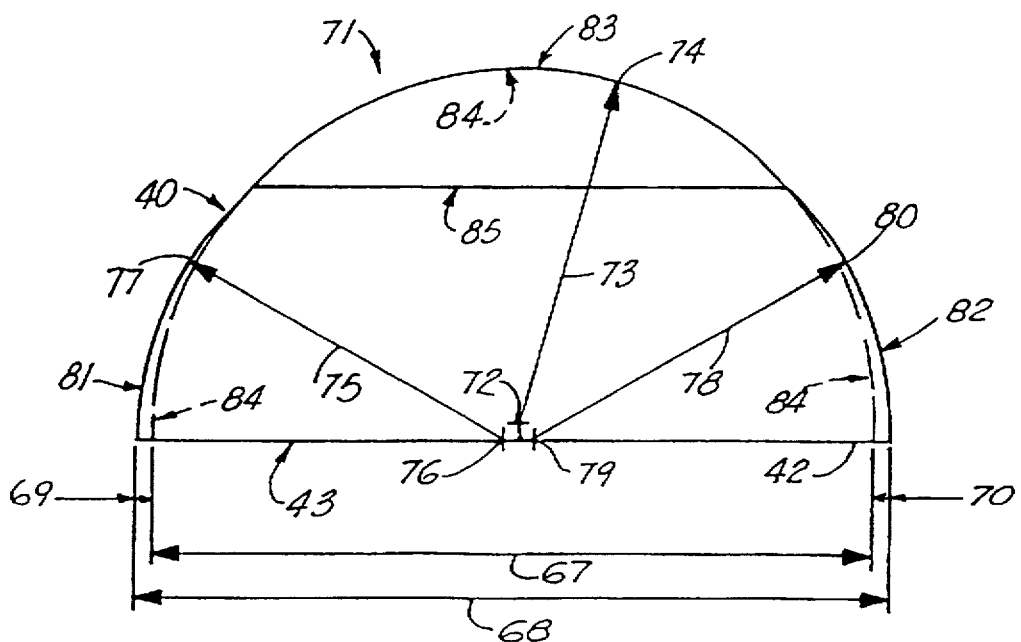
FIG. 3 is a side sectional view of a third embodiment of the apparatus of the present invention.

FIG. 3 shows a third embodiment of the apparatus of the present invention designated by the numeral 71. The cup body 71 is similar in shape to the cup shown in FIG. 2. It thus has an outer surface 40 that is convex and an annular rim 42 that defines a base plane 43. However, the configuration of surface 40 differs slightly from that of the embodiment of FIG. 2. As shown in FIG. 3, an origin 72 is shown for beginning the reference line 73 that also has a terminal 74. The origin 72 lies on a line extending the shortest distance between cup apex 83 and base plane 43. Origin 72 can be for example two millimeters above base plane 43. The radial line 73 tracks a curved surface 84. A second pair of reference lines in the form of radius 75 and radius 78 extend from beginning points 76, 79 respectively to terminal points 77, 80.

In the embodiment of FIG. 3, a curved line 81 is generated by rotation of radius 75 between plane 43 and annular reference line 85. Similarly, the radius 78 tracks a curved line 82 between plane 43 and annular line 85. In FIG. 3, the dimension lines 67 extends between end portions of the curved line 84 at plane 43. The dimension line 68 defines the outer diameter of cup body 71, at plane 43. The thickened area that forms an interference fit is likewise designated by the numerals 69, 70 as with the embodiment of FIG. 2.

Figure 6:
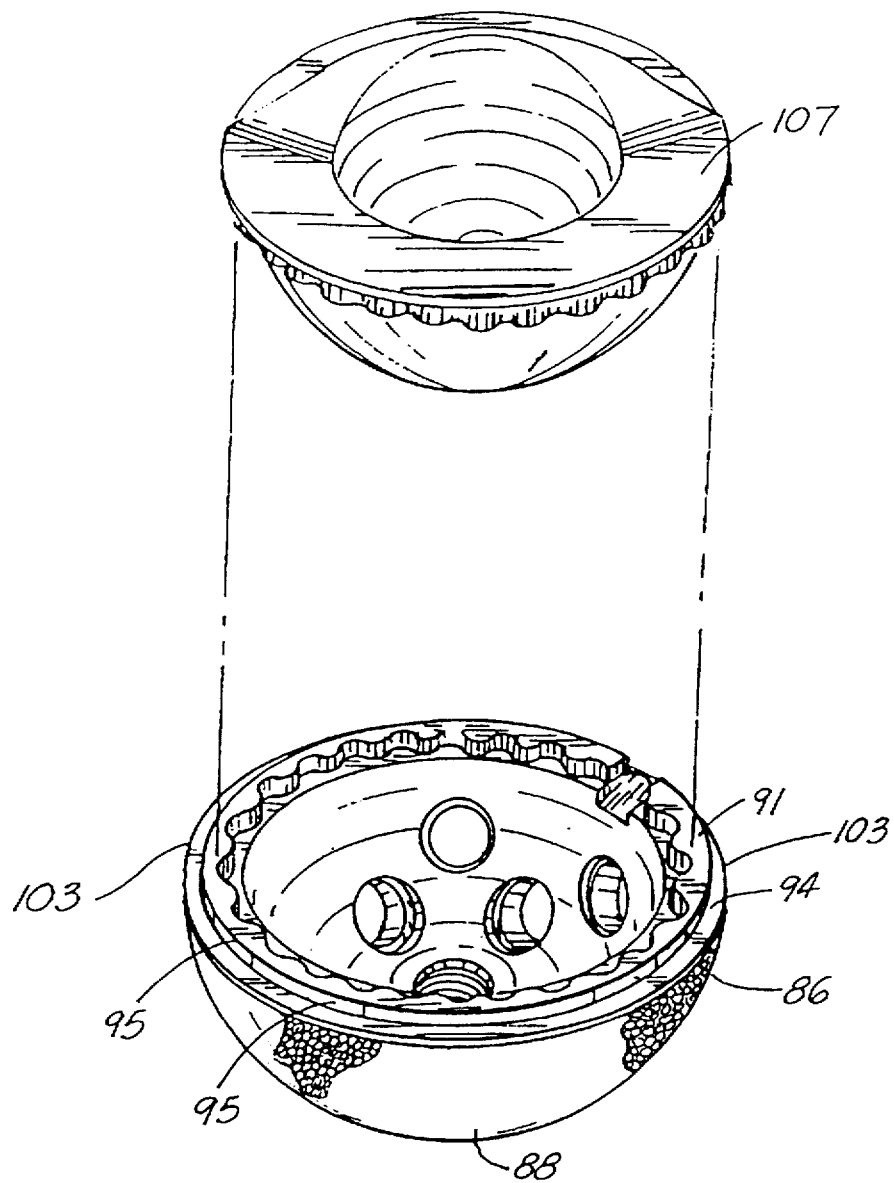
FIG. 6 is an exploded view of the embodiment of FIGS. 4-5.

In FIGS. 4–6, a fourth (and preferred) embodiment of the apparatus of the present invention is shown, designated by the numeral 86. In FIGS. 4–6, acetabular prosthesis 86 has an outer convex surface 87 that is comprised of two outer surface areas 88, 89. Surface 88 is a first annular surface area that is closest to cup apex 98. Surface 89 is a second annular surface that is closest to up base 91. The interface between surfaces 88, 89 is a smooth transition 90 as shown in FIG. 4. The smooth transition 90 is formed by generating the two surfaces 88, 89 using two different radii of curvature 100, 101 as described hereinafter.

Acetabular prosthesis 86 has a base 91 that defines a flat plane 92. Acetabular cup prosthesis 86 has a central axis 99 between apex 98 and arc center 97. The first annular surface area 88 is generated by a radial line 100 that has its origin at arc center 97. Radial line 100 generates a curved line 105, that extends from apex 98 to transition 90. The first convex surface area 88 is generated by rotating the curved line 105 three hundred sixty degrees (360°) about central axis 99.

The second annular surface area 89 is generated by a rotating curved line 106 three hundred sixty degrees (360°) about axis 99. Radial line 101 generates curved line 106 from periphery 103 to transition 90. The radius 101 is much smaller than the radius 100, being about sixty percent (60%) of the size of radius 100 for example. Arc centers 97, 102 are not in the same base plane 92, and are offset by a measure designated as 104.

This geometry of the embodiment of FIGS. 4–5 produce a generally hemispherical shape between apex 98 and transition 90, and a thicker annular section below transition 90. This geometry produces an improved interference fit with a hemispherically shaped surgically prepared socket reamed in the patient's acetabulum. The interference fit begins after the cup has been fitted about two thirds of the distance into the surgically reamed acetabular socket. The surgically prepared socket would be reamed with a hemispherical reamer having an outer hemispherical shape generated by a radial line equal to the size of radial line 100 and extending between apex 98 and shoulder 94. Thus, the surface area 89 will be oversized as compared to the surgically prepared hemispherical opening, the surface area 89 producing an interference fit with the patient's bone tissue upon full insertion of the prosthesis 86 into the surgically prepared hemispherical socket.

Annular shoulders 94, 95 intersect each other to form an angle of about ninety degrees (90°), forming annular recess 93. Shoulder 94 falls in plane 92. Shoulder 95 is perpendicular to plane 92. Recess 93 can accept tissue in-growth. A polyethylene cup liner 107 can snap into the cup body 86.

Figure 7:
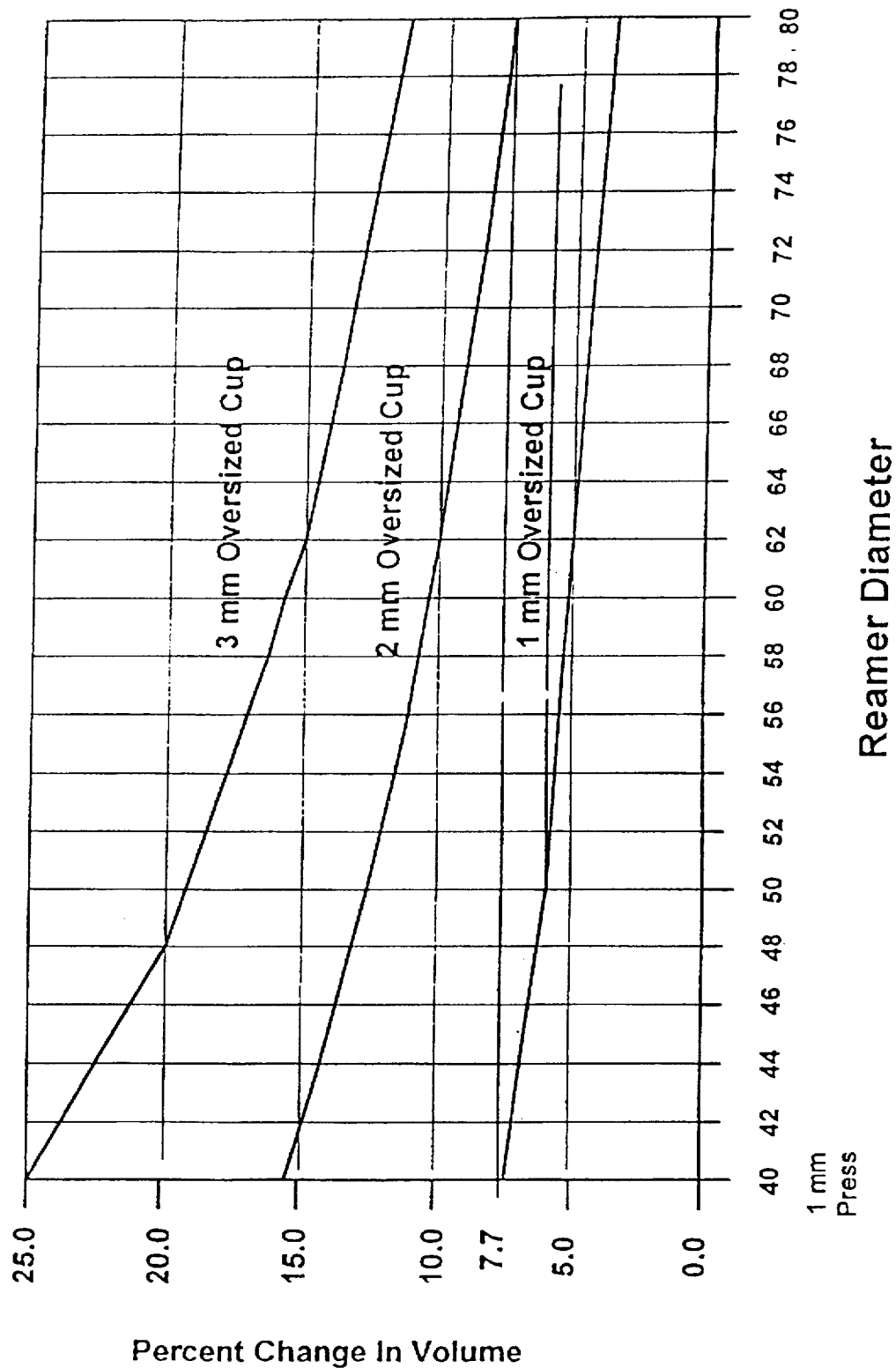
FIG. 7 is a schematic graphical illustration of the proportionality aspect of the present invention.

In FIG. 7 there is illustrated in graphical form a proportionality concept that can be applied to each apparatus of the present invention. FIG. 7 shows a comparison of the percent (%) change in volume with the reamer diameter used by the surgeon to create the hemispherically shaped reamed opening that could be occupied with a hemispherical shell.

Three different curves 108–110 are shown. The curve 108 is for a one millimeter (1 mm) oversized cup. The curve 109 is for a two millimeters (2 mm) oversized cup. The curve 110 is for a three millimeters (3 mm) oversized cup. With the teaching of the present invention, a cup has the same percentage change in volume notwithstanding the reamed diameter. This means that smaller cups require less press or interference fit while larger cups may accommodate more interference fit.

The following Table I lists examples of cup diameters and the proportional sizing of the present invention:

TABLE I

| Cup Reamed Diameter in Millimeters | % Change in Dia. | Peripheral Press Or Interference Fit In Millimeters |
| --- | --- | --- |
| 40 | 11.68 | 1.50 |
| 42 | 11.10 | 1.50 |
| 44 | 10.58 | 1.50 |
| 46 | 10.45 | 1.55 |
| 48 | 10.34 | 1.60 |
| 50 | 10.23 | 1.65 |
| 52 | 10.13 | 1.70 |
| 54 | 10.04 | 1.75 |
| 56 | 9.96 | 1.80 |
| 58 | 9.88 | 1.85 |
| 60 | 9.80 | 1.90 |
| 62 | 9.74 | 1.95 |
| 64 | 9.67 | 2.00 |
| 66 | 9.61 | 2.05 |
| 68 | 9.55 | 2.10 |
| 70 | 9.50 | 2.15 |
| 72 | 9.45 | 2.20 |
| 74 | 9.40 | 2.25 |
| 76 | 9.36 | 2.30 |

This proportionality can be calculated by dividing the difference in volume of the cup and the acetabulum by the volume of the acetabulum (the $V_c-V_a)/V_a$. When calculated over a range of cup sizes (for example, forty millimeters (40 mm)–eighty millimeters (80 mm)), one can see that the percent change in volume is approximately the same for a forty millimeters (40 mm) cup pressed at one millimeter (1 mm) as an eighty millimeters (80 mm) cup pressed at two millimeters (2 mm). This is illustrated in the percentage change in volume vs. reamer diameter graph of FIG. 7. The percent change in volume of the bone may also be expressed in terms of diameter and can be calculated by the following: $\Delta V=(D_{cup}^3-D_{reamer}^3)/D_{reamer}^3$, wherein $\Delta V$=change in volume, $D_{cup}$=diameter of acetabular cup prosthesis, $D_{reamer}$=diameter of reamer.

Figure 8:
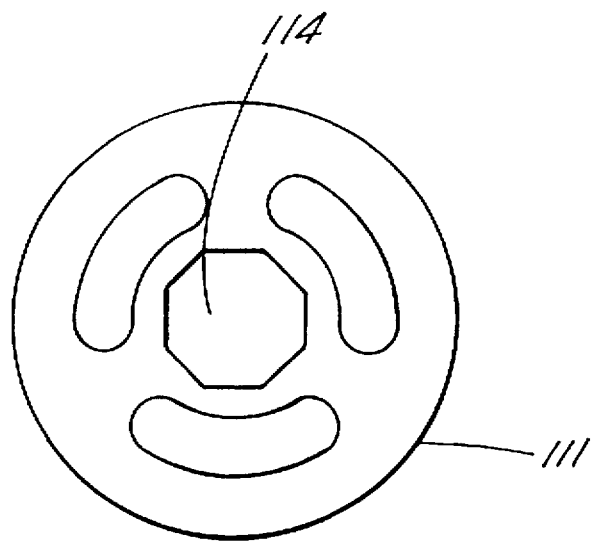
FIGS. 8-9 are driver top and side views of the reamer instrument portion of the apparatus of the present invention.
Figure 9:
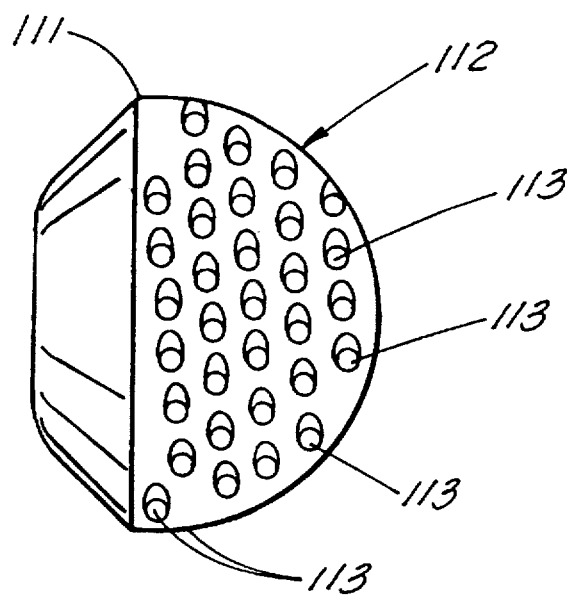

In FIGS. 8–9, reamer 111 is shown in the form of a cutting head having outer hemispherical surface 112 covered with an array of regularly spaced cutting elements 113. Drive socket 114 accepts a suitable rotary drive tool.

If the same millimeter increment in cup oversizing is inserted into different acetabula, such as a two millimeter (2 mm) oversized fifty millimeter (50 mm) cup in a forty eight millimeter (48 mm) acetabulum, and a two millimeter (2 mm) oversized seventy millimeter (70 mm) cup in a sixty eight millimeter (68 mm) acetabulum, a greater relative change in volume occurs in the smaller compared to the larger acetabulum. This produces greater bone strains in the smaller sized acetabulum.

With the same millimeter increment in cup oversizing, there is a greater risk of fracture in a small acetabulum and a greater risk of inadequate press fit stability in large acetabulum. A cup which is slightly widened at the periphery increases lateral bone strains more than an oversized hemispherical cup, with only a slight increase in medial bone strains. The non-hemispherical geometry of the present invention provides better peripheral stability than an oversized hemispherical cup and less risk of fracture through the dome of the acetabulum.

When a constant amount of oversizing is used, the relative change in volume is greater for a small diameter compared to a large diameter cup (see FIG. 7). For example, when the acetabulum is reamed to forty two millimeters (42 mm) and a two millimeter (2 mm) oversized (forty four millimeter (44 mm) diameter) cup is inserted, the acetabular volume increases by fifteen percent (15%). When the acetabulum is reamed to sixty two millimeters (62 mm) and a two millimeter (2 mm) oversized (sixty four millimeter (64) diameter) cup is inserted, the acetabular volume increase by ten percent (10%). Another example is that both a forty eight millimeter (48 mm) reamed acetabulum oversized by two millimeter (2 mm) and a seventy two millimeter (72 mm) reamed acetabulum oversized by three millimeter (3 mm) each produce a thirteen percent (13%) change in volume.

The following table lists the parts numbers and parts descriptions as used herein and in the drawings attached hereto.

| PARTS LIST | |
| --- | --- |
| Part Number | Description |
| 10 | acetabular cup prosthesis |
| 11 | convex surface |
| 12 | concavity |
| 13 | annular rim |
| 14 | base plane |
| 15 | concave surface |
| 16 | cup wall |
| 17 | origin |
| 18 | radial line |
| 19 | terminal |
| 20 | curved line |
| 21 | apex |
| 22 | reference line |
| 23 | radial line |
| 24 | beginning point |
| 25 | terminal |
| 26 | arrow |
| 27 | radial line |
| 28 | beginning point |
| 29 | terminal |
| 30 | arrow |
| 31 | curved line |
| 32 | beginning point |
| 33 | curved line |
| 34 | beginning point |
| 35 | arrow |
| 36 | arrow |
| 37 | arrow |
| 38 | arrow |
| 39 | acetabular cup prosthesis |
| 40 | convex surface |
| 41 | concavity |
| 42 | annular rim |
| 43 | base plane |

PARTS LIST -continued

| Part Number | Description |
|---|---|
| 44 | concave surface |
| 45 | cup wall |
| 46 | origin |
| 47 | radial line |
| 48 | terminal |
| 49 | curved line |
| 50 | apex |
| 51 | reference line |
| 52 | radial line |
| 53 | beginning point |
| 54 | terminal |
| 55 | arrow |
| 56 | radial line |
| 57 | beginning point |
| 58 | terminal |
| 59 | arrow |
| 60 | curved line |
| 61 | beginning point |
| 62 | curved line |
| 63 | beginning point |
| 64 | terminal |
| 65 | terminal |
| 66 | annular reference line |
| 67 | arrow |
| 68 | arrow |
| 69 | arrow |
| 70 | arrow |
| 71 | acetabular cup prosthesis |
| 72 | origin |
| 73 | radial line |
| 74 | terminal |
| 75 | reference line |
| 76 | beginning point |
| 77 | terminal |
| 78 | reference line |
| 79 | beginning point |
| 80 | terminal |
| 81 | curved line |
| 82 | curved line |
| 83 | apex |
| 84 | curved line |
| 85 | annular reference line |
| 86 | acetabular cup prosthesis |
| 87 | outer surface |
| 88 | first annular surface |
| 89 | second annular surface |
| 90 | smooth transition |
| 91 | base |
| 92 | plane of base |
| 93 | annular rim |
| 94 | annular shoulder |
| 95 | annular shoulder |
| 96 | concave surface |
| 97 | arc center |
| 98 | apex |
| 99 | axis |
| 100 | radius |
| 101 | radius |
| 102 | arc center |
| 103 | periphery |
| 104 | offset |
| 105 | curved line |
| 106 | curved line |
| 107 | cup liner |
| 108 | curve |
| 109 | curve |
| 110 | curve |
| 111 | reamer |
| 112 | hemispherical surface |
| 113 | cutting elements |
| 114 | drive socket |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of surgically implanting a selected one of a plurality of acetabular cup prostheses available in a surgical inventory in a patient's pelvis, comprising the steps of:

a) reaming the patient's acetabulum with a reamer to form a cup-shaped surgically prepared cavity;

b) filling the cup-shaped cavity with the selected one of the plurality of cup-shaped prostheses that is selected from an available surgical inventory, each prosthesis having an annular peripheral buildup portion that forms an interference fit with the pelvis at the cup-shaped cavity;

c) selecting the prosthesis from the plurality of available prostheses by measuring the diameter of the cavity to determine cup prosthesis diameter when selecting the prosthesis; and d) wherein in steps "b" and "c" the amount of peripheral buildup increases incrementally as cup diameter increases so that the ratio of the volume of the cup prosthesis and the volume of the cup-shaped cavity remain substantially the same for any one of the cup prosthesis selected.

2. A method of surgically implanting one of a plurality of acetabular cup prostheses available in a surgical inventory in a patient's pelvis, comprising the steps of:

a) reaming the patient's acetabulum with a reamer to form a cup-shaped surgically prepared cavity;

b) filling the cup-shaped cavity with one of a plurality of cup-shaped prostheses selected from an available surgical inventory, each prosthesis having an annular peripheral buildup portion that forms an interference fit with the pelvis at the cup-shaped cavity;

c) selecting the prosthesis from the plurality of available prostheses by measuring the diameter of the cavity to determine cup prosthesis diameter when selecting the prosthesis; and d) wherein in steps "b" and "c" of the amount of peripheral buildup increases incrementally as cup diameter increases so that the ratio of the peripheral diameter of the cup prosthesis and the diameter of the cup-shaped cavity remain substantially the same for any cup prosthesis selected.

3. The method of claim 1 wherein the plurality of available prostheses have diameters of between about 40 and 80 mm.

4. The method of claim 1 wherein the plurality of available prostheses are oversized in diameter in relation to the surgically prepared cavity a proportional volume for all cup diameters, wherein the amount of oversize falls in a range of between about 1 and 3 mm.

5. The method of claim 1 wherein the plurality of available prostheses are oversized in diameter in relation to the surgically prepared cavity a proportional diameter for all cup diameters, wherein the amount of oversize falls in a range of between about 1 and 3 mm.

6. The method of claim 1 wherein the plurality of available prostheses are oversized in volume in relation to the volume of the surgically prepared cavity by a constant volume measure that falls in a range of between about 9 and 12%.

7. The method of claim 2 wherein the plurality of available prostheses are oversized in volume in relation to the diameter of the surgically prepared cavity by a constant diameter measure that falls in a range of between about 9 and 12%.

8. The method of claim 1 wherein the plurality of available prostheses have diameters of between about 40 and 80 mm and the increase in diameter for each cup is in the range of between about 9 and 12%.

9. The method of claim 1 wherein the plurality of available prostheses have diameters of between about 40 and 80 mm and the amount of oversize press fit is about 9–12% of reamed cavity diameter.

10. The method of claim 1 wherein the cup body selected is selected from a plurality of prostheses that each have a diameter of about 9–12% the diameter of the reamed cavity.

11. The method of claim 1 wherein the cup body selected is selected from cup bodies that are between about 40 mm and 80 mm in diameter and with about the following listed oversize for press fit:

| Cup Reamed Diameter in Millimeters | % Change in Dia. | Peripheral Press Or Interference Fit In Millimeters |
| --- | --- | --- |
| 40 | 11.68 | 1.50 |
| 42 | 11.10 | 1.50 |
| 44 | 10.58 | 1.50 |
| 46 | 10.45 | 1.55 |
| 48 | 10.34 | 1.60 |
| 50 | 10.23 | 1.65 |
| 52 | 10.13 | 1.70 |
| 54 | 10.04 | 1.75 |
| 56 | 9.96 | 1.80 |
| 58 | 9.88 | 1.85 |
| 60 | 9.80 | 1.90 |
| 62 | 9.74 | 1.95 |
| 64 | 9.67 | 2.00 |
| 66 | 9.61 | 2.05 |
| 68 | 9.55 | 2.10 |
| 70 | 9.50 | 2.15 |
| 72 | 9.45 | 2.20 |
| 74 | 9.40 | 2.25 |
| 76 | 9.36 | 2.30 |

12. A method of surgically implanting one of a plurality of acetabular cup prostheses in a patient's pelvis, comprising the steps of;
   a) providing an inventory of a plurality of cup prostheses each having a cup diameter of between 40 mm and 80 mm, the inventory providing at least one cup with a diameter closer to 40 mm, at least one cup with a diameter closer to 80 mm and other cups with diameters at spaced intervals between 40 mm and 80 mm;
   b) reaming the patient's acetabulum with a reamer to form a surgically prepared cavity;
   c) filling the cavity with one of the plurality of available cup-shaped prostheses, each prosthesis having an oversized portion that forms an interference or press fit with the pelvis at the reamed cavity of the acetabulum;
   d) selecting the prosthesis from the plurality of available prostheses by first determining the size of the reamed cavity; and
   e) wherein in steps "c" and "d" the peripheral diameter of the selected cup body is greater than the diameter of the cavity substantially the same percentage range increase for each cup selected.

13. An acetabular prosthesis and instrumentation apparatus for enabling a surgeon to implant an acetabular prosthesis, comprising:
   a) a plurality of rotary reamer instruments, each having a cup-shaped reamer head with a rounded convex annular outer surface having cutting elements thereon, each said surface having a diameter;
   b) a plurality of prosthesis cup bodies, each having one of the reamer instruments as a correspondingly shaped companion reamer instrument, an inner concave surface and an outer convex surface, the convex surface shaped to register into a patient's acetabular socket that has been surgically prepared with the corresponding companion reamer instrument;
   c) wherein a selected companion reamer instrument enables the surgeon to ream the patient's acetabular socket to form a surgically prepared socket that corresponds in shape to the rounded annular shape of the selected reamer instrument cutting surface;
   d) wherein the diameter of a selected prosthesis cup body for each of the cup bodies is about 9–12 percent greater than the diameter of the surgically prepared socket that is prepared using the correspondingly shaped companion reamer instrument.

14. The acetabular prosthesis and instrumentation apparatus of claim 13 wherein the reamer instrument has an array of cutting elements spaced over the rounded annular surface.

15. The acetabular prosthesis and instrumentation apparatus of claim 1 wherein the cup bodies are each between 1 mm and 3 mm greater in diameter than the diameter of the companion reamer.

16. The acetabular prosthesis and instrumentation apparatus of claim 1 wherein each of the reamer instruments has a diameter of between 40 mm and 80 mm.

17. The acetabular prosthesis and instrumentation apparatus of claim 1 wherein the plurality of available cup body prostheses are oversized in diameter in relation to the respective surgically prepared cavity a generally proportional volume for all cup body diameters, wherein the amount of oversize falls in a range of between about 1 mm and 3 mm of oversize diameter.

18. The acetabular prosthesis and instrumentation apparatus of claim 1 wherein the plurality of available prostheses are oversized in diameter in relation to the surgically prepared cavity a generally proportional volume for all cup body diameters, and wherein the amount of peripheral press fit oversize falls in a range of between about 1 mm and 2 mm, and the reamed diameter is between about 40 mm and 64 mm.

19. The acetabular prosthesis and instrumentation apparatus of claim 1 wherein the plurality of available prostheses are oversized in diameter in relation to the surgically prepared cavity a generally proportional volume for all cup body diameters, and wherein the amount of peripheral press fit oversize falls in a range of between about 2 mm and 3 mm, and the reamed diameter is between about 64 mm and 80 mm.

20. The acetabular prosthesis and instrumentation apparatus of claim 1 wherein the oversize for press fit in millimeters is between 1.0 and 3.0 mm including at least a plurality of cup bodies having one or more diameters and with about the corresponding press fit in millimeters listed as follows:

| Cup Reamed Diameter in Millimeters | % Change in Dia. | Peripheral Press Or Interference Fit In Millimeters |
| --- | --- | --- |
| 40 | 11.68 | 1.50 |
| 42 | 11.10 | 1.50 |
| 44 | 10.58 | 1.50 |
| 46 | 10.45 | 1.55 |

-continued

| Cup Reamed Diameter in Millimeters | % Change in Dia. | Peripheral Press Or Interference Fit In Millimeters |
|---|---|---|
| 48 | 10.34 | 1.60 |
| 50 | 10.23 | 1.65 |
| 52 | 10.13 | 1.70 |
| 54 | 10.04 | 1.75 |
| 56 | 9.96 | 1.80 |
| 58 | 9.88 | 1.85 |
| 60 | 9.80 | 1.90 |
| 62 | 9.74 | 1.95 |
| 64 | 9.67 | 2.00 |
| 66 | 9.61 | 2.05 |
| 68 | 9.55 | 2.10 |
| 70 | 9.50 | 2.15 |
| 72 | 9.45 | 2.20 |
| 74 | 9.40 | 2.25 |
| 76 | 9.36 | 2.30 | and wherein the cup body selected is between 40 mm and 80 mm.

21. The acetabular prosthesis and instrumentation apparatus of claim 1 wherein plurality of available prostheses are oversized in diameter in relation to the surgically prepared cavity a generally proportional volume for all cup body diameters, and wherein the amount of peripheral press fit oversize falls in a range of between about 1.5 mm and 2.3 mm, and the reamed diameter is between about 40 mm and 80 mm.

22. An acetabular prosthesis and instrumentation apparatus, comprising:
 a) a plurality of reamer instruments each having a cutter head with a generally hemispherical outer surface with cutting elements on the hemispherical surface, said surface having a diameter;
 b) a plurality of corresponding, companion prosthesis cup bodies, each having an outer convex surface, the convex surface shaped to register into a patient's acetabular socket that has been surgically prepared with the reamer instrument;
 c) wherein the reamer instrument enables the surgeon to ream the patient's acetabular socket so that it is generally hemispherically shaped, corresponding in shape to the hemispherical shape of the reamer instrument cutting surface;
 d) each reamer instrument enabling the surgeon to form a socket for its corresponding companion cup body; and
 e) wherein the diameter of the companion prosthesis cup body for each of the cup bodies is about 9–12 percent greater than the diameter of the hemispherically shaped surgically prepared acetabular socket for a plurality of cup bodies.

* * * * *